United States Patent [19]

Sulc et al.

[11] Patent Number: 5,549,891
[45] Date of Patent: Aug. 27, 1996

[54] METHOD FOR DISINFECTING CONTACT LENS WITH CATALASE COMPOSITIONS

[75] Inventors: Jiri S. Sulc, Newport Beach; Zuzana Krcova, La Jolla, both of Calif.

[73] Assignee: Allergan, Irvine, Calif.

[21] Appl. No.: 223,340

[22] Filed: Apr. 5, 1994

[51] Int. Cl.⁶ ................................................. A61K 38/44
[52] U.S. Cl. .................. 424/94.4; 424/94.3; 424/458; 424/462; 424/468; 424/469; 424/471
[58] Field of Search ............................ 424/94.2, 94.3, 424/94.4, 458, 462, 464, 468, 469, 471; 435/177, 180, 182, 192

[56] References Cited

U.S. PATENT DOCUMENTS

| | | | |
|---|---|---|---|
| 3,282,702 | 7/1963 | Schreiner | 426/12 |
| 3,939,971 | 2/1976 | Tulis | 206/205 |
| 4,098,645 | 7/1978 | Hartdegen et al. | 435/182 |
| 4,119,580 | 10/1978 | Smith, Jr. et al. | 521/28 |
| 4,137,200 | 1/1979 | Wood et al. | 521/159 |
| 4,242,097 | 12/1980 | Rich, Jr. et al. | 436/100 |
| 4,265,634 | 5/1981 | Pohl | 436/161 |
| 4,269,306 | 5/1981 | Feniger | 206/5 |
| 4,314,823 | 2/1982 | Rich, Jr. et al. | 436/100 |
| 4,351,909 | 9/1982 | Stevens | 521/28 |
| 4,376,047 | 3/1983 | Christopher | 210/198.2 |
| 4,455,233 | 6/1984 | Pohl | 210/635 |
| 4,533,399 | 7/1985 | Mencke | 134/6 |
| 4,575,396 | 3/1986 | Matsumoto et al. | 134/7 |
| 4,655,957 | 4/1987 | Chromecek et al. | 252/174.23 |
| 4,757,014 | 7/1988 | Hendrickson et al. | 435/180 |
| 4,779,300 | 10/1988 | Pompe | 15/104.93 |
| 4,826,658 | 5/1989 | Kay | 422/30 |
| 4,829,001 | 5/1989 | Mencke et al. | 435/264 |
| 4,839,082 | 6/1989 | Bhatia | 252/174.12 |
| 4,855,234 | 8/1989 | Hendrickson et al. | 435/181 |
| 4,860,885 | 8/1989 | Kaufman et al. | 206/5.1 |
| 4,921,630 | 5/1990 | Bhatia | 252/174.12 |
| 5,000,962 | 3/1991 | Sangekar et al. | 424/482 |
| 5,011,661 | 4/1991 | Schafer et al. | 422/30 |
| 5,037,484 | 8/1991 | Su et al. | 134/7 |
| 5,054,610 | 10/1991 | Ajello | 206/51 |
| 5,088,146 | 2/1992 | Smith et al. | 15/104.94 |
| 5,089,053 | 2/1992 | Chou et al. | 134/7 |
| 5,089,240 | 2/1992 | Perlaky | 422/300 |
| 5,128,058 | 7/1992 | Ishii et al. | 252/174.13 |
| 5,190,760 | 3/1993 | Baker | 424/438 |
| 5,403,750 | 4/1995 | Braatz et al. | 436/531 |

FOREIGN PATENT DOCUMENTS

| | | |
|---|---|---|
| 0223479 | 5/1987 | European Pat. Off. . |
| 2314194 | 1/1977 | France . |
| 8607264 | 12/1986 | WIPO . |
| 9112825 | 9/1991 | WIPO . |

OTHER PUBLICATIONS

Derwent Publications Ltd., London, GB, 1978, See Abstract.

*Primary Examiner*—Michael G. Wityshyn
*Assistant Examiner*—Jean C. Witz
*Attorney, Agent, or Firm*—Frank J. Uxa

[57] ABSTRACT

Compositions and methods for destroying hydrogen peroxide in hydrogen peroxide-containing liquid aqueous media, for example, employed to disinfect contact lenses, are disclosed. In one embodiment, the present composition comprise at least one item containing a hydrophilic polyurethane component and a catalase component covalently bonded to the hydrophilic polyurethane component.

18 Claims, No Drawings

5,549,891

METHOD FOR DISINFECTING CONTACT LENS WITH CATALASE COMPOSITIONS

BACKGROUND OF THE INVENTION

This invention relates to catalase compositions useful for destroying hydrogen peroxide, for example, hydrogen peroxide used in disinfecting lenses, such as contact lenses. In particular, the invention relates to catalase compositions and methods useful to effectively destroy hydrogen peroxide and disinfect, and preferably clean, such lenses while reducing eye irritation caused by disinfecting the lenses, and to methods for producing such catalase compositions.

Contact lenses should be periodically disinfected and cleaned by the user to prevent infection or other deleterious effects on ocular health which may be associated with contact lens wear. Currently, there are several different conventional systems and methods which enable the user to clean and disinfect his/her contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses. However, residual hydrogen peroxide on a disinfected contact lens may cause irritation, burning or trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens. Liquid media (not including the hydrogen peroxide contained therein) used to disinfect contact lenses should be substantially isotonic, for example, to the human eye, and preferably ophthalmically acceptable so as to reduce the chances of problems caused by placing the disinfected lenses in the wearer's eyes.

Catalase has been effectively used to promote the destruction of residual hydrogen peroxide contact lens disinfectant. Kay U.S. Pat. No. 4,826,658 discloses disinfecting contact lenses with hydrogen peroxide in the presence of catalase immobilized on the container used to disinfect the lenses. Kay discloses that the catalase is absorbed, adsorbed, or chemically, e.g., covalently, bonded to a support material, such as alumina, bentonite, calcium phosphate gels, carbon, plastics (such as polystyrene, epoxy resins, methacrylates and methacrolates), carboxymethyl cellulose, carboxymethylsephadex, collagen, glass and silica gel, with polystyrene activated by gamma irradiation, U.V. light or corona discharge being preferred. The absorbed or adsorbed catalase is subject to being lost in the disinfecting medium and may contaminate the disinfected lenses. Many of the support materials disclosed by Kay are hydrophobic in nature and may inhibit the hydrogen peroxide-containing liquid aqueous medium from ever effectively contacting the catalase. This can result in incomplete destruction of hydrogen peroxide and irritation of, or even damage to, the eye wearing the disinfected lens. In other instances, the immobilized catalase is immediately exposed to the hydrogen peroxide-containing aqueous liquid medium so that the contact lens may not be effectively disinfected before being placed in the eye. Further, relatively sophisticated and complex processing, for example, as noted above, is often required to covalently bond the catalase to the support materials disclosed in the Kay patent.

There continues to be a need for a system which is relatively easy to produce, and effectively disinfects a contact lens and completely destroys the residual hydrogen peroxide disinfectant without contaminating the lens so that the disinfected lens can be safely and comfortably worn.

SUMMARY OF THE INVENTION

New compositions for destroying hydrogen peroxide, new methods for using such compositions, for example, in disinfecting contact lenses, and methods for producing such compositions have been discovered. The present compositions provide an effective, preferably controlled, driving force, preferably a diffusional driving force, to urge hydrogen peroxide-containing liquid aqueous medium to be in intimate contact with a catalase component so that the hydrogen peroxide is effectively and completely destroyed. In addition, the present compositions are preferably structured so that the hydrogen peroxide-containing liquid aqueous medium is substantially prevented from being exposed to the catalase component for a period of time after the composition is introduced into the liquid medium. This "delayed exposure" period of time allows the hydrogen peroxide to perform its function, for example, to disinfect the contact lens, before being destroyed.

The present compositions are relatively easy to produce, for example, can be produced using procedures which are employed to produce the substrate or support hydrophilic material. The catalase component, which is covalently bonded to the substrate or support hydrophilic material, preferably provides delayed destruction of hydrogen peroxide relative to catalase present in the liquid medium because, for example, of the time needed for diffusion of hydrogen peroxide into the substrate or support hydrophilic material. The catalase component is preferably covalently bonded to the substrate during the process of forming the substrate. This feature eliminates the need for any other treatment to immobilize the catalase, and greatly simplifies the present methods of producing hydrogen peroxide destroying compositions. Also, if, as is preferred, the substrate is a hydrophilic polyurethane foam, the foaming medium may include a surfactant which can be used as a detergent for lens cleaning. Other components may be added to the foaming medium if desired, such as a color indicator of hydrogen peroxide decomposition and the like.

The present system preferably eliminates tableting and/or the use of large amounts of auxiliary compounds necessary for tableting and tablet coating, and prevents catalase transfer into the eye without requiring that the disinfected contact lens be rinsed. The present compositions may be employed in the form of a disc (analogous to a tablet or pill), in the form of a plurality of particles, in the form of a swab, or may be part of a contact lens holder or case.

In one broad aspect, the present invention is directed to compositions which comprise at least one item containing a hydrophilic polyurethane component and a catalase component covalently bonded to the hydrophilic polyurethane component. This polyurethane component is preferably cross-linked and insoluble in water, in particular in a liquid aqueous medium containing hydrogen peroxide. The catalase component is preferably effective to cause the destruction of all the hydrogen peroxide present in this liquid aqueous medium to which the catalase component is exposed. The hydrophilic polyurethane component is preferably derived from one or more isocyanate-capped polyoxyalkylene polyols. Such polyols preferably include isocyano groups which react with amino groups present in the catalase to covalently bond the catalase component to the hydrophilic polyurethane component.

The present hydrophilic polyurethane component-containing compositions are preferably structured to substantially prevent the catalase component from being exposed to the hydrogen peroxide-containing liquid aqueous medium for a period of time after the composition is introduced into the liquid aqueous medium. This "delayed exposure" feature of the present invention can be achieved by controlling diffusion into the polyurethane component. For example, the extent of crosslinking of the polyurethane component can be controlled, e.g., increased, to control, e.g., increase, the resistance to diffusion within the polyurethane component. This controlled diffusion results in substantially preventing the catalase component from being exposed to the hydrogen peroxide-containing aqueous medium (HPLM) for a period of time after the catalase component/polyurethane component combination is introduced into the liquid medium. In addition, or alternately, the at least one item can include a barrier coating located relative to the catalase component so as to be effective to substantially prevent the catalase component from being exposed to the liquid aqueous medium for a period of time after the at least one item is introduced into the liquid aqueous medium. The "diffusion" controlled (or controlled diffusion) delayed exposure feature is preferred since no additional components (e.g., coating components) are needed and since no such additional components can contaminate the liquid medium containing the disinfected lens. Thus, this "controlled diffusion" delayed exposure feature is one important advantage of the present invention.

In another broad aspect of the present invention, a composition is provided which comprises at least one item containing a hydrophilic polymeric component and a catalase component covalently bonded to the hydrophilic polymeric component. The catalase component is effective to cause the destruction of hydrogen peroxide present in a liquid aqueous medium to which the catalase component is exposed. The hydrophilic polymeric component is insoluble in the liquid aqueous medium, and is preferably cross-linked. The composition is structured to substantially prevent the catalase component from being exposed to the liquid aqueous medium for a period of time after the at least one item is introduced into the liquid aqueous medium. In one embodiment, the at least one item includes a barrier coating located relative to the catalase component so as to be effective to substantially prevent the catalase component from being exposed to the liquid aqueous medium for a period of time after the at least one item is introduced into the liquid aqueous medium.

In a further broad aspect of the present invention, methods for producing a hydrogen peroxide destroying composition useful for destroying residual hydrogen peroxide in a hydrogen peroxide-containing liquid aqueous medium are provided. These methods comprise subjecting a precursor composition of a cross-linked polyurethane to effective curing conditions in the presence of an aqueous medium containing catalase. This subjecting step is effective to cause the reaction between amino groups of the catalase and isocyano groups of the polyurethane precursor composition thereby covalently bonding the catalase component to the polyurethane polymer component. In addition, this subjecting step is preferably effective to form a hydrophilic polyurethane component. One substantial advantage of this method is that the covalent bonding of the catalase component occurs at substantially the same time as the hydrophilic polyurethane component is formed. No further processing and no further catalysts are required.

In a still further embodiment of the present invention, methods of disinfecting a lens, preferably a contact lens, are provided. Such methods comprise contacting a lens to be disinfected with a hydrogen peroxide-containing liquid aqueous medium at effective lens disinfecting conditions to thereby disinfect the lens. The hydrogen peroxide-containing liquid aqueous medium is contacted with a composition comprising at least one item, as described above, containing a covalently bonded catalase component. This catalase component is effective to cause the destruction of the hydrogen peroxide, preferably of all the hydrogen peroxide, present in the hydrogen peroxide-containing liquid aqueous medium (HPLM).

These and other aspects and advantages of the present invention will become apparent in the detailed description and claims.

DETAILED DESCRIPTION OF THE INVENTION

The present invention is of value where hydrogen peroxide is used to disinfect all types of lenses, e.g., contact lenses, which are benefitted by periodical disinfecting. Such lenses may be made of any suitable material or combination of materials and may have any suitable configuration not substantially deleteriously affected by hydrogen peroxide, the present compositions or the present methods.

The present compositions are effective to destroy hydrogen peroxide in a hydrogen peroxide-containing liquid aqueous medium (HPLM). In general, the present compositions comprise at least one item containing a hydrophilic polymeric component, preferably a hydrophilic polyurethane component, and a catalase component covalently bonded to the hydrophilic polymeric component.

The catalase component is effective to cause the destruction of hydrogen peroxide present in a liquid aqueous medium to which the catalase component is exposed. The amount of catalase component employed is preferably sufficient to destroy all the hydrogen peroxide present in the HPLM to which the catalase component is exposed. Excess amounts, for example, up to about 300% of the amount required for complete destruction of the hydrogen peroxide present, of catalase component may be employed. Catalase component is preferably present in an amount of about 10 to about 1000, more preferably about 20 to about 800, international units of catalase activity per milliliter of liquid medium.

The hydrophilic polymeric component is preferably insoluble in the liquid aqueous medium. In this manner, the catalase component is maintained separate and apart from the contact lens or other items which might be present in the liquid aqueous medium.

Although any suitable hydrophilic polymeric component may be employed in accordance with the present invention, it is preferred that the polymeric component be derived from a polymer selected from the group consisting of polyurethanes, cross-linked polyvinyl pyrrolidone, hydroxyalkyl acrylate polymers, hydroxyalkyl methacrylate polymers, collagen, and mixtures thereof.

In a particularly useful embodiment, the hydrophilic polymeric component comprises a hydrophilic polyurethane component, more preferably derived from one or more isocyanate-capped polyalkylene polyols. Such polyols, hereinafter referred to as prepolymers, can be produced using conventional and well known processing techniques. For example, see Wood et al U.S. Pat. No. 4,137,200 which is incorporated in its entirety herein by reference.

Briefly, such prepolymers are prepared by capping polyoxyalkylene, in particular polyoxyethylene, glycols having a reactive functionality equal to 2 with a molar excess of a diisocyanate which leads to an isocyanate-capped polyurethane product (A) having an isocyanate functionality of 2. A polyol, such as pentaerythritol, having a reactive functionality equal to 4 is reacted with a large molar excess of a diisocyanate to form an isocyanate-capped polyurethane intermediate product (B) having an isocyanate functionality of 4. By blending the two isocyanate-capped products thus prepared, that is products (A) and (B), in various molar proportions, the resulting product mixture has an average isocyanate functionality greater than two and on treatment with aqueous reactants containing catalase results in hydrophilic cross-linked polyurethane foams including a covalently bonded catalase component in accordance with the present invention. In addition, other monomeric or polymeric polyisocyanate cross-linking agents may be substituted for the tetraisocyanate product (B). Tolylene-2,4,6-triisocyanate, having a reactive functionality of 3, is an example of a simple monomeric triisocyanate which may be usefully employed to achieve the same objective of imparting to the system an average isocyanate functionality greater than 2.

Care should be taken so that the capped product has a reaction functionality greater than 2 even after considering that the amine or amino group of the catalase reacts with an isocyano group on the capped product. Alternately, the capped product and/or aqueous reactant may contain a suitable crosslinking agent, if desired, in which the case the capped product may have a functionality approximating 2.

The amount of crosslinking provided for in the hydrophilic polymeric component may be controlled so as to control the rate of diffusion of the hydrogen peroxide-containing liquid aqueous medium into the final foamed product. This "controlled diffusion" feature of the present invention can be used to control the rate at which the catalase component causes the destruction of the hydrogen peroxide present in the aqueous liquid medium, for example, so that a contact lens present in the HPLM can be effectively disinfected before destroying the hydrogen peroxide. For example, this "controlled diffusion" feature can delay exposing meaningful amounts of hydrogen peroxide to catalase bonded to the hydrophilic polymeric component from at least about 1 minute or about 5 minutes, and preferably from about 5 minutes to about 30 minutes, after the composition is first introduced into a HPLM. At the same time, the rate of diffusion should be sufficiently high to result in complete destruction of the residual hydrogen peroxide in the liquid aqueous medium in a reasonable time, for example, in about 4 hours or about 3 hours or less after the present composition is first introduced into the HPLM. The use of a hydrophilic polymeric component in this embodiment of the present invention allows for an effective, preferably controlled, positive driving force so that the hydrogen peroxide in the liquid aqueous medium can be intimately and effectively contacted with the catalase component to destroy the hydrogen peroxide.

Another approach to control the rate of destruction of hydrogen peroxide present in the HPLM is to control the surface area of the hydrophilic polymeric component. In general, the larger the surface area of the hydrophilic polymeric material the higher the rate of hydrogen peroxide destruction. The surface area of the hydrophilic polymeric component can be controlled, for example, by controlling the materials present and/or the conditions employed during the production of the hydrophilic polymeric component. If a hydrophilic polyurethane component, such as described above, is employed, its surface area can be controlled by controlling the amount and/or type of surfactant component included during foaming.

In an additional approach, the at least one item can include a barrier coating located relative to the catalase component so as to be effective to substantially prevent the catalase component from being exposed to the liquid aqueous medium for a period of time after the at least one item is first introduced into the liquid aqueous medium. The "controlled diffusion", "controlled surface area" and "barrier coating" features of the present invention can be used alone or in any combination with each other.

In the present invention, hydrogen peroxide is preferably used in a disinfecting amount. A disinfecting amount preferably means such amount as will reduce the microbial burden by one log order in three hours. More preferably, the amount of hydrogen peroxide used is such that the microbial load is reduced by one log order in one hour. Particularly preferred are those amounts which reduce the microbial load by one log order in 10 minutes or less. Aqueous hydrogen peroxide solutions, preferably containing about 0.5% to about 6% of hydrogen peroxide, are known to be effective disinfecting solutions for contact lenses. These solutions are effective at killing bacteria and fungi and other microorganisms which may be found on contact lenses.

The liquid media used are selected to have no substantial detrimental effect on the lens being treated, and on the wearer of the treated lens. The liquid media are constituted to allow, and preferably to even facilitate, the present lens treatment or treatments. The liquid media are preferably aqueous-based and more preferably are substantially isotonic and/or ophthalmically acceptable (without consideration of the hydrogen peroxide which may be present) liquid aqueous media. A material is said to be "ophthalmically acceptable" when it is compatible with ocular tissue, that is causes no significant or undue detrimental effect when brought into contact with ocular tissue. The liquid media preferably include as effective amount of a tonicity adjusting component to provide the liquid media with the desired tonicity. Particularly useful aqueous liquid media are those derived from saline, e.g., a conventional saline solution or buffered saline solution. During the disinfecting contacting, it is preferred that the aqueous liquid medium have a pH in the range of about 2 or 3 to about 9. During the time in which the residual hydrogen peroxide disinfectant is being destroyed, the pH of the aqueous liquid medium is preferably about 3 or higher, for example, to about 10, or about 6 to about 8.

The liquid media, e.g., liquid aqueous media, employed preferably include a buffer component which is present in an amount effective to maintain the pH of the liquid medium in the desired range. This buffer component may be present in the liquid medium and/or may be introduced into the liquid medium. Among the suitable buffer components or buffering agents which may be employed are those which are conventionally used in contact lens care products. Examples of useful buffer components include those with carbonate functionalities, bicarbonate functionalities, phosphate functionalities, borate functionalities, and the like and mixtures thereof. The buffers may be alkali metal and alkaline earth metal salts, in particular sodium and potassium.

In one embodiment, solid compositions, which are preferably initially contacted with (first introduced into) the HPLM at substantially the same time as is the lens to be disinfected, can provide for effective lens disinfection and, in addition, effectively destroy the residual hydrogen peroxide remaining in the liquid medium so that the disinfected lens can be removed from the liquid medium and placed into the eye for safe and comfortable wear. Such solid compositions may be present in the form of at least one item, e.g., tablet, pill, capsules, one or more solid particles, granules and the like, which is structured, as described elsewhere herein, to delay the exposure of the catalase component to the hydrogen peroxide in the HPLM.

The delayed exposure of the catalase component to the hydrogen peroxide in the HPLM may be accomplished by "controlled diffusion" structuring of the at least one item and/or by including a barrier component (e.g., delayed release coating) on the at least one item.

A barrier component may be provided by coating a core tablet, pill, granules or other particle or particles or the like, containing the catalase component/hydrophilic polymeric component combination with a slow dissolving coating material, which may ultimately be completely or only partially soluble in the liquid medium. The delayed exposure form of the catalase component is preferably such that substantially no effective exposure of the catalase component to the hydrogen peroxide in the HPLM occurs during the delay period followed by rapid and substantially complete exposure of the catalase component at the end of or after the delay period.

Barrier components suitable as either coatings or as matrices, include water soluble vinyl polymers, such as polyvinylpyrollidone, polyvinylalcohol and polyethyleneglycol; water soluble proteins; polysaccharide and cellulose derivatives, such as methyl cellulose, hydroxypropylmethyl cellulose, sodium carboxymethyl cellulose; alginic acid and its salts and other derivatives; and the like and mixtures thereof.

Although multi-layered (including core and coating layers) tablets or pills are preferred, the delayed release form of the present compositions can be present in any other suitable item or items, such as masses of powders, granules and the like. Delayed release technology which may be employed to provide for delayed exposure of the catalase component, is well known in the art as exemplified by the text *Controlled Drug Delivery*, 2nd Ed., Joseph R. Robinson & Vincent H. L. Lee, Eds., Marcel Dekker, Inc., N.Y., 1987.

The amount of barrier component used is not critical in the present invention provided that such barrier component functions as described herein. The barrier component or components may suitably be present in the range of about 1% or about 5% to about 1000% or more, based on the weight of the catalase component.

The present solid compositions may be produced using any one of many suitable methods, a number of which are conventional and well known in the art. The production method chosen depends, in large measure, on the desired form of the composition. For example, the at least one item can be molded or cut or otherwise shaped into the desired form.

The present compositions may further include at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et. al. U.S. Reissue Pat. No. 32,672 and Karageozian et al U.S. Pat. No. 3,910,296 are useful in the present invention. These patents are incorporated in their entirety by reference herein. Among the useful enzymes are those selected from proteolytic enzymes, lipases and mixtures thereof. Preferred proteolytic enzymes are those which are substantially free of sulfhydryl groups or disulfide bonds, whose presence may react with the active oxygen in the HPLM to the detriment of the activity of the enzyme. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two sub-classes, subtilisin A and subtilisin B. In the subtilisin A grouping are enzymes derived from such species are *B. subtilis*, *B. licheniformis* and *B. pumilis*. Organisms in this sub-class produce little or no neutral protease or amylase. The subtilisin B sub-class is made up of enzymes from such organisms a *B. subtilis, B. subtilis* var. amylosacchariticus, *B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

The present solid compositions which include such lens cleaning enzymes may be structured to release the enzyme in the liquid medium which contacts the composition at any time relative to the other component or components of the composition provided that the released enzyme is effective at the conditions present in the liquid medium to perform the cleaning function, as described herein. In one particularly useful embodiment, the cleaning enzyme is released in the liquid medium prior to or at substantially the same time as the catalase component is exposed to the hydrogen peroxide in the HPLM.

Using the present compositions to disinfect a contact lens may be accomplished by contacting the lens to be disinfected with the composition, if the composition includes a liquid medium, or with a combination of the composition and a liquid medium at conditions effective to effectively disinfect the lens.

In the event that a debris removing enzyme is present in the composition, the contact lens in the liquid medium is also effectively cleaned of such debris. This cleaning action can occur before the lens is disinfected, at the time the lens is being disinfected, or after the lens is disinfected.

It is preferred that the catalase component not be exposed to the hydrogen peroxide in the HPLM until the lens has been contacted with, e.g., immersed in, the HPLM for a time sufficient, more preferably in the range of about 1 minute to about 4 hours and still more preferably in the range of about 5 minutes to about 1 hour, to effectively disinfect the lens. It is also preferred that substantially all of the residual hydrogen peroxide in the liquid medium be destroyed in less than about 3 hours or about 4 hours, more preferably in less than about 1 hour after the catalase component is initially exposed to the hydrogen peroxide in the HPLM.

The disinfecting contacting preferably occurs in a quantity, e.g., about 5 ml to about 15 ml, of an HPLM at a temperature to maintain the liquid medium substantially liquid. It is preferred that the contacting temperature be in the range of about 0°C. to about 100° C., and more preferably in the range of about 10° C. to about 60° C. and still more preferably in the range of about 15° C. to about 30° C. Contacting at or about ambient temperature is very convenient and useful. The contacting preferably occurs for a time to effectively disinfect the lens being treated.

The catalase component, preferably after the disinfecting contacting, is exposed to the hydrogen peroxide in the HPLM to destroy the residual hydrogen peroxide. This "hydrogen peroxide destruction" contacting can occur at the same temperature conditions at which the disinfecting contacting occurred. This contacting occurs for a time sufficient to destroy all the hydrogen peroxide present in the liquid medium. The catalase component may be present in a "controlled diffusion" form and/or in a "barrier component" delayed release form, as described elsewhere herein. After being exposed to the catalase component, the liquid medium preferably includes substantially no hydrogen peroxide, and the disinfected lens can be removed from this liquid medium and placed directly into the eye for safe and comfortable wear. Alternately, the disinfected lens can be rinsed, e.g., with saline solution, for example, to free the lens of cleaning enzyme or enzymes, prior to placing the disinfected lens into the eye.

The following non-limiting examples illustrate certain aspects of the present invention.

EXAMPLES 1 TO 3

A prepolymer derived from polyoxyethylene glycol, trimethylolpropane and toluene diisocyanate sold by W. R. Grace and Co. under the trademark Hypol is selected. This prepolymer is combined with an aqueous mixture containing water, a conventional ethylene oxide/propylene oxide block copolymer surface active agent (sold by BASF under the trademark Pluronic F-127) and catalase. This combination is allowed to foam at room temperature into articles of various shapes. The hydrophilic polyurethane foam that is prepared from this combination exhibits good physical properties.

In one run, identified as Form A, the foam is molded or cut into the form of a disc which conveniently fits in the bottom of a conventional container used to disinfect contact lenses. This disc includes 1000 international units of catalase activity in the form of a covalently bonded catalase component.

In another run, identified as Form B, the foam is cast in the form of a swab which can be conveniently placed in a conventional container used to disinfect contact lenses. This swab includes 1000 international units of catalase activity in the form of a covalently bonded catalase component.

In another run, identified as Form C, the foam is cast into a liner which can be conveniently adhesively adhered to and partially cover the inner sidewall of a conventional container used to disinfect contact lenses. This liner includes 1000 international units of catalase activity in the form of a covalently bonded catalase component.

EXAMPLE 4

10 ml of a substantially isotonic aqueous solution containing 3% w/v of hydrogen peroxide is provided in a container at room temperature. The contact lens to be disinfected and the hydrophilic foam disc, Form A, are placed in the solution at the same time. Three (3) hours after the contact lens is first introduced into the solution, it is removed from the solution and placed into the wearer's eye. It is found that the contact lens is effectively disinfected and that all of the hydrogen peroxide originally present in the solution is destroyed during this three (3) hour period. The lens wearer experiences no discomfort or eye irritation from wearing the disinfected contact lens.

EXAMPLE 5

10 ml of a substantially isotonic aqueous solution containing 3% (w/v) of hydrogen peroxide is provided in a container at room temperature. The contact lens to be disinfected and the hydrophilic foam swab, Form B, are placed in the solution at the same time. Three (3) hours after the contact lens is first introduced into the solution, it is removed from the solution and placed into the wearer's eye. It is found that the contact lens is effectively disinfected and that all the hydrogen peroxide originally present in the solution is destroyed within this three (3) hour period of time. The lens wearer experiences no discomfort or eye irritation from wearing the disinfected contact lens.

EXAMPLE 6

10 ml of a substantially isotonic aqueous solution containing 3% (w/v) of hydrogen peroxide is provided at room temperature in a container equipped with the liner of hydrophilic foam material, Form C. The contact lens to be disinfected is placed in the solution at substantially the same time the solution is introduced into the container. Three (3) hours after the contact lens is first introduced into the solution, it is removed from the solution and placed into the wearer's eye. It is found that the contact lens is effectively disinfected. In addition, substantially all the hydrogen peroxide originally present in the solution is destroyed within this three (3) hour period of time. The lens wearer experiences no discomfort or eye irritation from wearing the disinfected contact lens.

EXAMPLES 7 TO 9

Examples 4 to 6 are each repeated several times using the same disc, Form A, the same swab, Form B, and the same liner, Form C. After each repetition, the results are substantially as set forth in Examples 4 to 6, respectively.

EXAMPLES 10 TO 12

Examples 1 to 3 are repeated except that an additional increment of cross-linking agent is included in the combination. The resulting foams include covalently bonded catalase component, as set forth in Examples 1 to 3. In addition, the hydrophilic foams are more extensively cross-linked than the corresponding foams identified in Examples 1 to 3. The increased degree of cross-linking effectively prevents a hydrogen peroxide-containing liquid medium from contacting the catalase component covalently bonded to the hydrophilic foam for a period of time on the order of about 0.5 to 1 hour after the form is initially contacted with the hydrogen peroxide-containing liquid medium.

EXAMPLES 13 TO 15

Examples 4 to 6 are repeated except that the foams produced in Examples 10 to 12, respectively, are used in place of the corresponding foams in Examples 4 to 6.

In each case, the hydrogen peroxide concentration of the solution remains substantially constant for a period of time on the order of about 30 minutes after the hydrophilic foam is initially introduced into the solution. Thereafter, the concentration of hydrogen peroxide is reduced and, ultimately, in a period of time of about four (4) hours after the foam is initially contacted with the hydrogen peroxide-containing solution, substantially all of the hydrogen peroxide originally present in the solution is destroyed.

In each case, at the end of this four (4) hour period of time, the contact lens is found to be effectively disinfected. The disinfected contact lens is then removed from the solution and placed into the wearer's eye. The lens wearer experiences no discomfort or eye irritation from wearing the disinfected contact lens.

EXAMPLE 16

The disc produced in Example 1 (that is the disc identified as Form A) is used to produce a layered item. The core of this layered item is Form A, and is surrounded by a delayed release layer. This layered item has the following composition.

| Form A | 1000 Units of Catalase Activity |
|---|---|
| Hydroxypropyl-methyl cellulose (delayed release layer) | 8 mg |

This layered item is used to disinfect a conventional soft contact lens as follows.

10 ml of a substantially isotonic aqueous solution containing 3% (w/v) hydrogen peroxide is provided in a container at room temperature. The contact lens to be disinfected and the layered item are placed in the solution at the same time. For approximately 45 minutes, the solution remains substantially quiet, i.e., substantially no bubbling (gas evolution) takes place. For the next approximately two (2) hours, the solution bubbles. After this period of time, the solution becomes and remains quiet. Four (4) hours after the contact lens is first introduced into the solution, it is removed from the solution and placed into the wearer's eye. It is found that the contact lens is disinfected, and that all the hydrogen peroxide originally present in the solution has been destroyed. Also, the lens wearer experiences no discomfort or eye irritation from wearing the disinfected contact lens. The bubbling of the solution provides an indication that hydrogen peroxide destruction is occurring. An indication that the peroxide destruction is complete is provided when the bubbling stops.

The present invention provides a very convenient and safe "one-step" contact lens disinfection system. The use of covalently bonded catalase component allows the system user to disinfect his/her lens and destroy residual peroxide while avoiding contaminating his/her eyes with catalase. Also, the "delayed exposure" feature of the present invention allows the user to exercise a substantial degree of control over the disinfecting of this/her lens. The "controlled diffusion" feature of this invention provides this enhanced degree of disinfection control advantageously without adding extraneous components, for example, coating or barrier components to the disinfecting medium.

While this invention has been described with respect to various specific examples and embodiments, it is to be understood that the invention is not limited thereto and that it can be variously practiced within the scope of the following claims.

What is claimed is:

1. A method of disinfecting a lens comprising the steps of:
   (1) contacting a lens with a hydrogen peroxide-containing liquid aqueous medium at effective lens disinfecting conditions, thereby disinfecting said lens; and
   (2) contacting said hydrogen peroxide-containing liquid aqueous medium with a composition comprising at least one item containing a hydrophilic polyurethane which is cross-linked and catalase covalently bonded to said hydrophilic polyurethane and being effective to cause the destruction of hydrogen peroxide present in a liquid aqueous medium to which said catalase is exposed, said step (2) being effective to cause the destruction of all of the hydrogen peroxide present in said hydrogen peroxide-containing liquid aqueous medium, said hydrophilic polyurethane being insoluble in said hydrogen peroxide-containing liquid aqueous medium, said composition being effective to substantially prevent said catalase from being exposed to said hydrogen peroxide-containing liquid aqueous medium for a controlled period of time after said composition is initially contacted with said hydrogen peroxide-containing liquid aqueous medium, provided that the resistance to diffusion within said hydrophilic polyurethane is controlled to control the length of said controlled period of time.

2. The method of claim 1 wherein said hydrophilic polyurethane is derived from one or more isocyanate-capped polyoxyalkylene glycols.

3. The method of claim 1 wherein said hydrophilic polyurethane is produced by subjecting a precursor composition of said hydrophilic polyurethane to effective curing conditions in the presence of an aqueous medium containing catalase to form said hydrophilic polyurethane and to covalently bond said catalase to said hydrophilic polyurethane.

4. The method of claim 3 wherein said precursor composition includes one or more isocyanate-capped polyoxyalkylene glycols.

5. The method of claim 4 wherein said one or more isocyanate-capped polyoxyalkylene glycols include functional isocyano groups and said catalase includes functional amine groups, and said subjecting is effective to react said functional isocyano groups with said functional amine groups to covalently bond said catalase to said hydrophilic polyurethane.

6. The method of claim 1 wherein said at least one item includes a barrier coating located relative to said catalase so as to be effective to substantially prevent said hydrophilic polyurethane from being exposed to said liquid aqueous medium for a period of time after said at least one item is introduced into said liquid aqueous medium.

7. The method of claim 1 wherein the degree to which said hydrophilic polyurethane is cross-linked is controlled to control the resistance to diffusion within said hydrophilic polyurethane.

8. The method of claim 1 wherein said controlled period of time is sufficiently long to allow said lens to be disinfected by said hydrogen peroxide-containing liquid aqueous medium.

9. A method of disinfecting a contact lens comprising the steps of:

(1) contacting a contact lens with a hydrogen peroxide-containing liquid aqueous medium at effective disinfecting conditions, thereby disinfecting said contact lens; and (2) contacting said hydrogen peroxide-containing liquid aqueous medium with a composition free of a barrier coating and comprising at least one item containing a hydrophilic polymer having a resistance to diffusion and catalase covalently bonded to said hydrophilic polymer and being effective to cause the destruction of hydrogen peroxide present in a liquid aqueous medium to which said catalase is exposed, said step (2) being effective to cause the destruction of all of the hydrogen peroxide present in said hydrogen peroxide-containing liquid aqueous medium, said hydrophilic polymer being effective to substantially prevent said catalase from being exposed to said hydrogen peroxide-containing liquid aqueous medium for a predetermined period of time after said hydrophilic polymer is initially contacted with said hydrogen peroxide-containing liquid aqueous medium, said predetermined period of time being controlled by controlling the resistance to diffusion within said hydrophilic polymer.

10. The method of claim 9 wherein said predetermined period of time is sufficient to allow said contact lens to be disinfected by said hydrogen peroxide-containing liquid aqueous medium.

11. The method of claim 9 wherein said hydrophilic polymer is cross-linked and the resistance to diffusion within said hydrophilic polymer is controlled by controlling the degree of cross-linking of said hydrophilic polymer.

12. The method of claim 9 wherein said predetermined period of time is in the range of about 5 minutes to about 30 minutes.

13. The method of claim 12 wherein said catalase causes the destruction of all the hydrogen peroxide present in said hydrogen peroxide-containing liquid aqueous medium in about 3 hours or less after said composition is initially contacted with said hydrogen peroxide-containing liquid aqueous medium.

14. The method of claim 9 wherein said hydrophilic polymer is a hydrophilic polyurethane which is cross-linked.

15. The method of claim 14 wherein said hydrophilic polyurethane is derived from one or more isocyanate-capped polyoxyalkylene glycols.

16. The method of claim 14 wherein said hydrophilic polyurethane is produced by subjecting a precursor composition of said hydrophilic polyurethane to effective curing conditions in the presence of an aqueous medium containing catalase to form said hydrophilic polyurethane and to covalently bond said catalase to said hydrophilic polyurethane.

17. The method of claim 16 wherein said precursor composition includes one or more isocyanate-capped polyoxyalkylene glycols.

18. The method of claim 17 wherein said one or more isocyante-capped polyoxyalkylene glycols include functional isocyano groups and said catalase includes functional amine groups, and said subjecting is effective to react said functional isocyano groups with said functional amine groups to covalently bond said catalase to said hydrophilic polyurethane.

* * * * *